United States Patent
Sweitzer

(10) Patent No.: US 11,723,672 B2
(45) Date of Patent: Aug. 15, 2023

(54) CHUCK ASSEMBLY FOR A MEDICAL DEVICE

(71) Applicant: Shukla Medical, St. Petersburg, FL (US)

(72) Inventor: Zachary Robert Sweitzer, Keyport, NJ (US)

(73) Assignee: Shukla Medical, St. Petersburg (FI)

( * ) Notice: Subject to any disclaimer, the term of this patent is extended or adjusted under 35 U.S.C. 154(b) by 288 days.

(21) Appl. No.: 17/029,435

(22) Filed: Sep. 23, 2020

(65) Prior Publication Data

US 2021/0290253 A1    Sep. 23, 2021

Related U.S. Application Data

(60) Provisional application No. 62/991,160, filed on Mar. 18, 2020.

(51) Int. Cl.
*A61B 17/16* (2006.01)
*A61B 17/00* (2006.01)

(52) U.S. Cl.
CPC ........ *A61B 17/162* (2013.01); *A61B 17/1633* (2013.01); *A61B 2017/00477* (2013.01)

(58) Field of Classification Search
CPC ............... A61B 17/16; A61B 17/1613; A61B 17/1615; A61B 17/1617; A61B 17/162; A61B 17/1622; A61B 17/1624; A61B 17/1626; A61B 17/1628; A61B 17/1633
See application file for complete search history.

(56) References Cited

U.S. PATENT DOCUMENTS

| | | | | |
|---|---|---|---|---|
| 5,888,200 | A  * | 3/1999 | Walen ....................... | B25F 3/00 606/167 |
| 6,780,189 | B2 * | 8/2004 | Tidwell .............. | A61B 17/1633 606/80 |
| 7,011,661 | B2 * | 3/2006 | Riedel ................. | B23B 31/1072 606/80 |
| 7,066,940 | B2 * | 6/2006 | Riedel .............. | A61B 17/32002 606/167 |
| 8,801,713 | B2 * | 8/2014 | del Rio ................ | A61B 17/162 279/78 |
| 9,113,917 | B2 * | 8/2015 | del Rio ............ | A61B 17/32002 |
| 9,381,023 | B2 * | 7/2016 | del Rio ............ | A61B 17/32002 |

(Continued)

FOREIGN PATENT DOCUMENTS

| | | |
|---|---|---|
| WO | 2012138338 A1 | 10/2012 |
| WO | 2016081604 A2 | 5/2016 |
| WO | 2019092615 A1 | 5/2019 |

OTHER PUBLICATIONS

International Search Report dated Jun. 11, 2021 in International Patent Application No. PCT/US2021/022333.

(Continued)

*Primary Examiner* — Eric S Gibson
(74) *Attorney, Agent, or Firm* — Kim IP Law Group LLC

(57) ABSTRACT

A chuck assembly for a medical device is provided. The chuck assembly includes a mounting base structured to couple to a tool; a housing coupled to the mounting base; and a cam sleeve within the housing and movable with respect to the housing between a locked position and an unlocked position, the cam sleeve having an annular base, an arm extending from the annular base, and a cam extending laterally from the arm.

21 Claims, 11 Drawing Sheets

(56) References Cited

U.S. PATENT DOCUMENTS

| | | | |
|---|---|---|---|
| 9,414,848 B2* | 8/2016 | Edwards | A61B 17/162 |
| 9,681,879 B2* | 6/2017 | del Rio | A61B 17/1617 |
| 10,702,284 B2* | 7/2020 | Högerle | B25B 23/141 |
| 10,987,112 B2* | 4/2021 | del Rio | A61B 17/32002 |
| 2003/0130663 A1* | 7/2003 | Walen | A61B 17/1615 |
| | | | 606/167 |
| 2012/0259337 A1* | 10/2012 | del Rio | A61B 17/162 |
| | | | 29/428 |
| 2021/0290253 A1* | 9/2021 | Sweitzer | A61B 17/1633 |

OTHER PUBLICATIONS

Written Opinion dated Jun. 11, 2021 in International Patent Application No. PCT/US2021/022333.

* cited by examiner

CHUCK ASSEMBLY FOR A MEDICAL DEVICE

CROSS REFERENCE TO RELATED APPLICATIONS

The present application claims the benefit of U.S. Provisional Patent Application No. 62/991,160 filed Mar. 18, 2020 entitled "Twist Lock Chuck," the entire disclosure of which is hereby incorporated herein by reference.

BACKGROUND OF THE INVENTION

Exemplary embodiments of the subject disclosure relate generally to chuck assemblies for medical devices, and more specifically, to chuck assemblies for receiving and locking various medical device accessories.

Chuck assemblies for use with various medical devices are known. Such assemblies operate to receive and lock various accessories (such as tool bits) for use in medical procedures. Typical chuck assemblies are bulky and difficult to operate, sometimes requiring numerous, cumbersome steps to insert, lock and remove an accessory. There is thus a need for a chuck assembly and accessory that overcome these and other disadvantages of the prior art.

BRIEF SUMMARY OF THE INVENTION

In accordance with various exemplary embodiments of the subject disclosure, a chuck assembly and associated accessory are provided. The chuck assembly enables a quick and simplified locking ability whereby the accessory may be inserted and locked within the chuck in a single "push-to-lock" motion. Various exemplary embodiments also provide low-profile chuck assemblies that are capable of withstanding substantial compression and tension loads.

In accordance with an exemplary embodiment of the subject disclosure, a chuck assembly for a medical device is provided. The chuck assembly includes a mounting base structured to couple to a tool; a housing coupled to the mounting base; and a cam sleeve within the housing and movable with respect to the housing between a locked position and an unlocked position, the cam sleeve having an annular base, an arm extending from the annular base, and a cam extending laterally from the arm.

In accordance with another aspect of the subject disclosure, the cam includes a distally facing helical camming surface.

In accordance with still another aspect of the subject disclosure, the helical camming surface extends annularly about five to twenty degrees.

In accordance with yet another aspect of the subject disclosure, the cam includes a proximally facing locking surface.

In accordance with still another aspect of the subject disclosure, the proximal locking surface extends annularly about five to twenty degrees.

In accordance with yet another aspect of the subject disclosure, the housing includes internal guide rails and the annular base includes a distally facing locking surface, and in which the proximally facing locking surface, the distally facing locking surface and the guide rails form a cavity for receiving and securing a guide tab of an accessory.

In accordance with still another aspect of the subject disclosure, the chuck assembly further includes a biasing member biasing the cam sleeve into the locked position.

In accordance with yet another aspect of the subject disclosure, the cam sleeve is rotationally movable within the housing.

In accordance with still another aspect of the subject disclosure, the cam sleeve includes another arm extending from the annular base.

In accordance with yet another aspect of the subject disclosure, the chuck assembly further includes a dial engaged with the cam sleeve for moving the cam sleeve between the locked position and unlocked position.

In accordance with still another aspect of the subject disclosure, the dial circumscribes the housing.

In accordance with yet another aspect of the subject disclosure, the housing comprises an overall diameter of about 0.635 to 1.905 cm.

In accordance with still another aspect of the subject disclosure, the housing is formed integrally with the mounting base.

In accordance with another exemplary embodiment of the subject disclosure, a medical device is provided. The medical device includes a chuck assembly having a mounting base structured to couple to a tool, a housing coupled to the mounting base; and a cam sleeve within the housing and movable with respect to the housing between a locked position and an unlocked position, the cam sleeve having an annular base, an arm extending from the annular base, and a cam extending laterally from the arm; and an accessory having a mounting shaft structured to be received within the housing, and a mounting tab extending from the shaft and structured to be engaged by and retained within the housing by the cam sleeve.

In accordance with yet another aspect of the subject disclosure, the mounting tab is a linear tab extending substantially parallel to a longitudinal axis of the mounting shaft.

In accordance with still another aspect of the subject disclosure, the mounting shaft includes a working end structured to engage a fixture.

In accordance with yet another aspect of the subject disclosure, when the accessory is inserted into the housing and the cam sleeve is in the locked position, the mounting tab directly engages the arm.

In accordance with still another aspect of the subject disclosure, when the accessory is inserted into the housing and the cam sleeve is in the locked position, the mounting tab is bounded by internal guide rails of the housing, a proximally facing locking surface of the cam and a distally facing locking surface of the annular base.

In accordance with yet another exemplary embodiment of the subject disclosure, a medical device is provided. The medical device includes a chuck assembly having a mounting base structured to couple to a tool, a housing coupled to the mounting base, and a cam sleeve within the housing and rotatable with respect to the housing between a locked rotational position and an unlocked rotational position, the cam sleeve having an annular base, a first arm extending from the annular base, the first arm including a first cam extending laterally from the first arm, the first cam having a first distally facing helical camming surface and a first proximally facing locking surface, and a second arm extending from the annular base and diametrically opposed from the first arm, the second arm including a second cam extending laterally from the second arm, the second cam having a second distally facing helical camming surface and a second proximally facing locking surface; and an accessory releasably engageable with the chuck assembly, the accessory including a mounting shaft structured to be received within the housing, and a mounting tab extending from the mounting shaft and structured to be engaged by and retained within the housing by the cam sleeve.

BRIEF DESCRIPTION OF THE SEVERAL VIEWS OF THE DRAWINGS

The following detailed description of an exemplary embodiment of the subject disclosure will be better understood when read in conjunction with the appended drawings. For the purpose of illustrating the present disclosure, there is shown in the drawings an exemplary embodiment. It should be understood, however, that the subject application is not limited to the precise arrangements and instrumentalities shown.

DETAILED DESCRIPTION OF THE INVENTION

Figure 1:
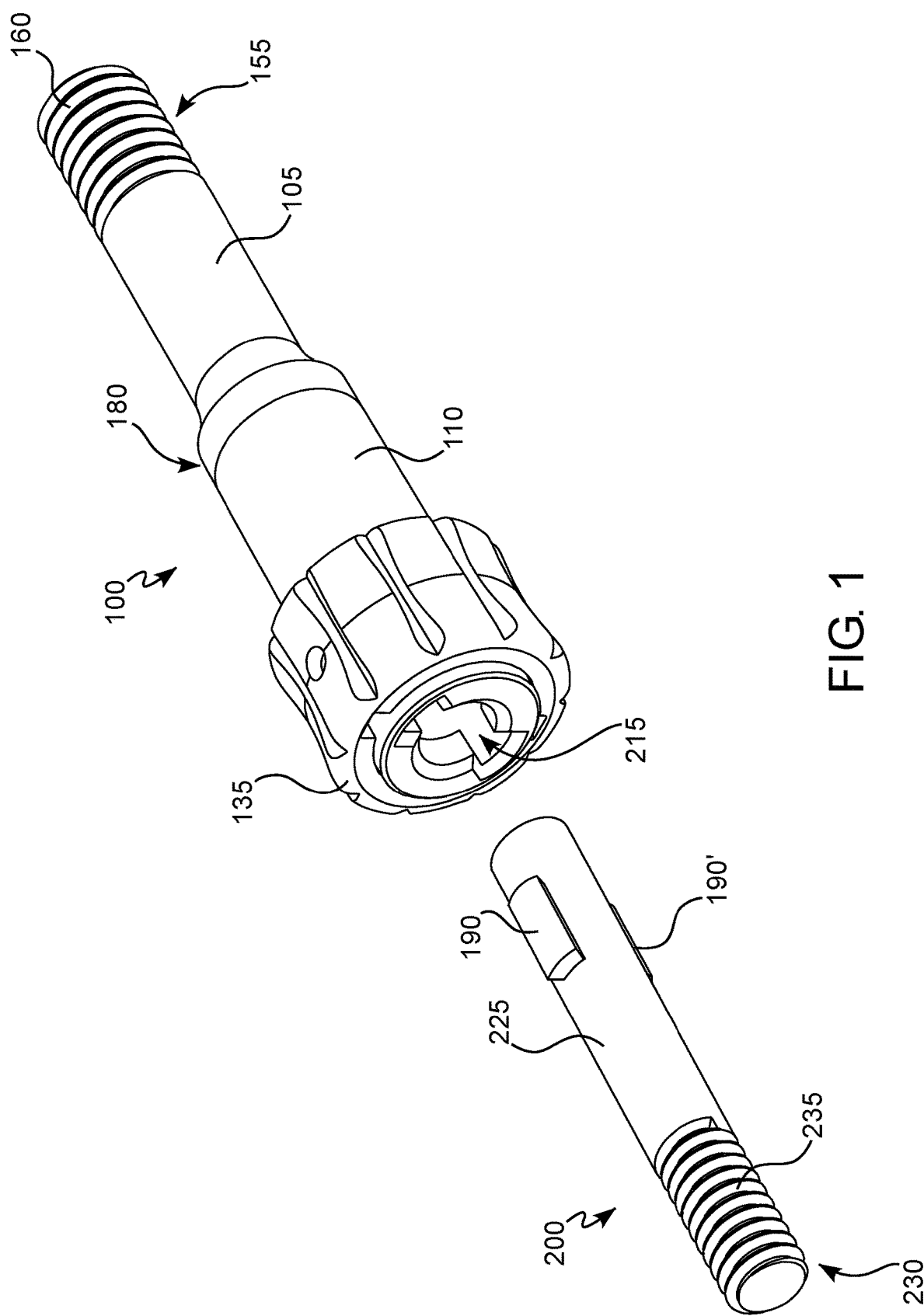
FIG. 1 is a perspective view of a chuck assembly and an accessory in accordance with an exemplary embodiment of the subject disclosure.
Figure 2:
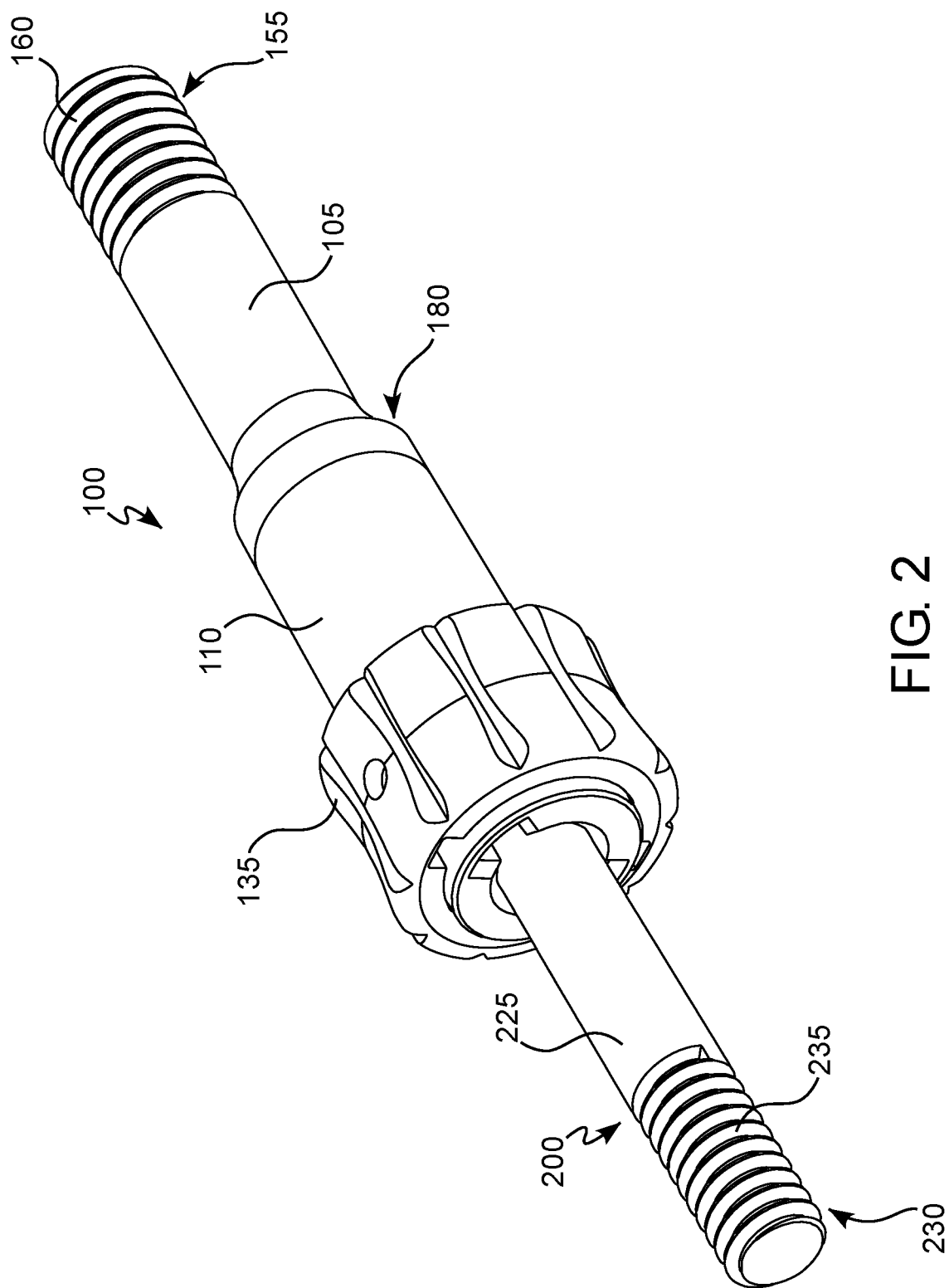
FIG. 2 is a perspective view of the chuck assembly of FIG. 1 with an inserted accessory.

Reference will now be made in detail to an exemplary embodiment of the subject disclosure illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as upper, lower, top, bottom, above, below and diagonal, are used with respect to the accompanying drawings. Such directional terms used in conjunction with the following description of the drawings should not be construed to limit the scope of the subject disclosure in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

"Substantially" as used herein shall mean considerable in extent, largely but not wholly that which is specified, or an appropriate variation therefrom as is acceptable within the field of art.

"Exemplary" as used herein shall mean serving as an example.

Throughout the subject application, various aspects thereof can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more exemplary embodiments. One skilled in the relevant art will recognize, in light of the description herein, that the subject disclosure can be practiced without one or more of the specific features or advantages of a particular exemplary embodiment. In other instances, additional features and advantages may be recognized in certain exemplary embodiments that may not be present in all exemplary embodiments of the present disclosure.

Referring now to FIGS. 1 through 9, there is shown an exemplary chuck assembly 100 in accordance with the subject disclosure. The chuck assembly 100 includes a mounting base 105, a housing 110 coupled rigidly to a distal end 180 of the base 105, a cam sleeve 120 rotatably positioned within the housing 110, a biasing member 145 with connecting ends 150, 150' (e.g., a torsion spring) operatively engaged with the mounting base 105 and the cam sleeve 120, stop pins 125, 125' coupled to the cam sleeve 120 and extending respectively through opposite sides of the housing 110, and a dial 135 circumscribing the housing 110 and coupled to the stop pins 125, 125'.

As more fully described below, the chuck assembly 100 is operable to receive and lock therein various accessories/fixtures, such as, for example, an extractor blade, tool bit, drill bit, saw blade, punch, intermediate connector, etc. An intermediate connector accessory 200, for example, is depicted in FIGS. 1 through 4. The accessory 200 includes a mounting shaft 225 having a locking tab and preferably two locking tabs 190, 190' and a working end 230 provided, e.g., with screw threads 235 for coupling to an interchangeable or disposable fixture (not shown). In alternative exemplary embodiments, the working end is provided with additional or alternative structures for coupling to a fixture. In still other exemplary embodiments, the accessory is formed integrally with a specific fixture.

Referring now to FIGS. 3, 4, 5A, 5B, 8A, 8B and 9, the housing 110 is cylindrical in shape and includes a distally facing guide slot 215, a plurality of inner guide rails 220 and stopper slots 130, 130' with respective first ends 165, 165' and second ends 170, 170' extending respectively through opposite sides of the housing 110.

As best shown in FIGS. 1-4, the mounting base 105 is coupled to the proximal end of the housing 110 and includes a distal end 180 provided with a biasing slot 175' and a proximal mounting end 155 having a fastener, e.g., screw threads 160 for coupling the chuck assembly 100 to a tool (not shown), such as, for example, an extractor, a drill, a jigsaw, etc. It should be appreciated that the mounting base 105 and the housing 110 may be formed integrally (such as, for example, as one piece or via laser welding of the base 105 and housing 110) and that the mounting end 155 of the mounting base 105 may include additional or alternative structures for coupling the chuck assembly 100 to a tool, and that various exemplary embodiments of the subject disclosure are not intended to be limited to any specific mounting structure(s). It should also be appreciated that the mounting base 105 (as well as other components of the chuck assembly 100) may be constructed from any materials suitable for an intended application, such as, for example, metal, wood, composites, polymers, disposable materials, etc., though various exemplary embodiments are not intended to be limited to any particular material or combination of materials.

As best shown in FIGS. 3, 4, 6C, and 7A through 9, the cam sleeve 120 is positioned to rotate freely within the housing 110 adjacent the distal end 180 of the mounting base 105. The cam sleeve 120 includes an annular base 245 provided with distally facing locking surfaces 197, 197' and at least one biasing slot 175, a central channel 210, and two arms 240, 240' extending distally from the annular base 245, though a single arm or more than two arms may be employed. The arms 240, 240' include laterally extending cams 250, 250' having respective proximally facing locking surfaces 195, 195' which, together with the distally facing locking surfaces 197, 197' and the guide rails 220 of the housing 110, form respective locking cavities 205, 205' (see FIGS. 8A and 8B) that tightly secure the locking tabs 190, 190' of the accessory 200 to prevent longitudinal and rotational displacement of the accessory when the mounting shaft 225 is fully inserted into the central channel 210 of the cam sleeve 120. The cams 250, 250' also include helical camming surfaces 185, 185' positioned to engage respectively with the locking tabs 190, 190' when the mounting shaft 225 is initially inserted into the central channel 210. In the exemplary embodiment depicted in the FIGS., the camming surfaces 185, 185' are helical and extend annularly about the central channel 210 to ensure that the locking tabs 190, 190' engage the camming surfaces 185, 185' smoothly and maintain a continuous line of contact with the camming surfaces 185, 185' as the mounting shaft 225 is inserted into the central channel 210. That is, the helical shape of each camming surface 185, 185' ensures that approximately the entire width "W" of the camming surface maintains contact with the respective locking tab 190, 190' as the mounting shaft 225 is inserted axially within chuck assembly 100. In one exemplary embodiment, the camming surfaces 185, 185' extend annularly about five to twenty degrees (e.g., 5, 10, 15, or 20 degrees), though the camming surfaces 185, 185' of other exemplary embodiments are not limited to extending any specific annular distance. Smooth contact between the locking tabs 190, 190' and the camming surfaces 185, 185' may be further facilitated by providing the locking tabs 190, 190' with fillets for engaging the camming surfaces 185, 185'.

Figure 3:
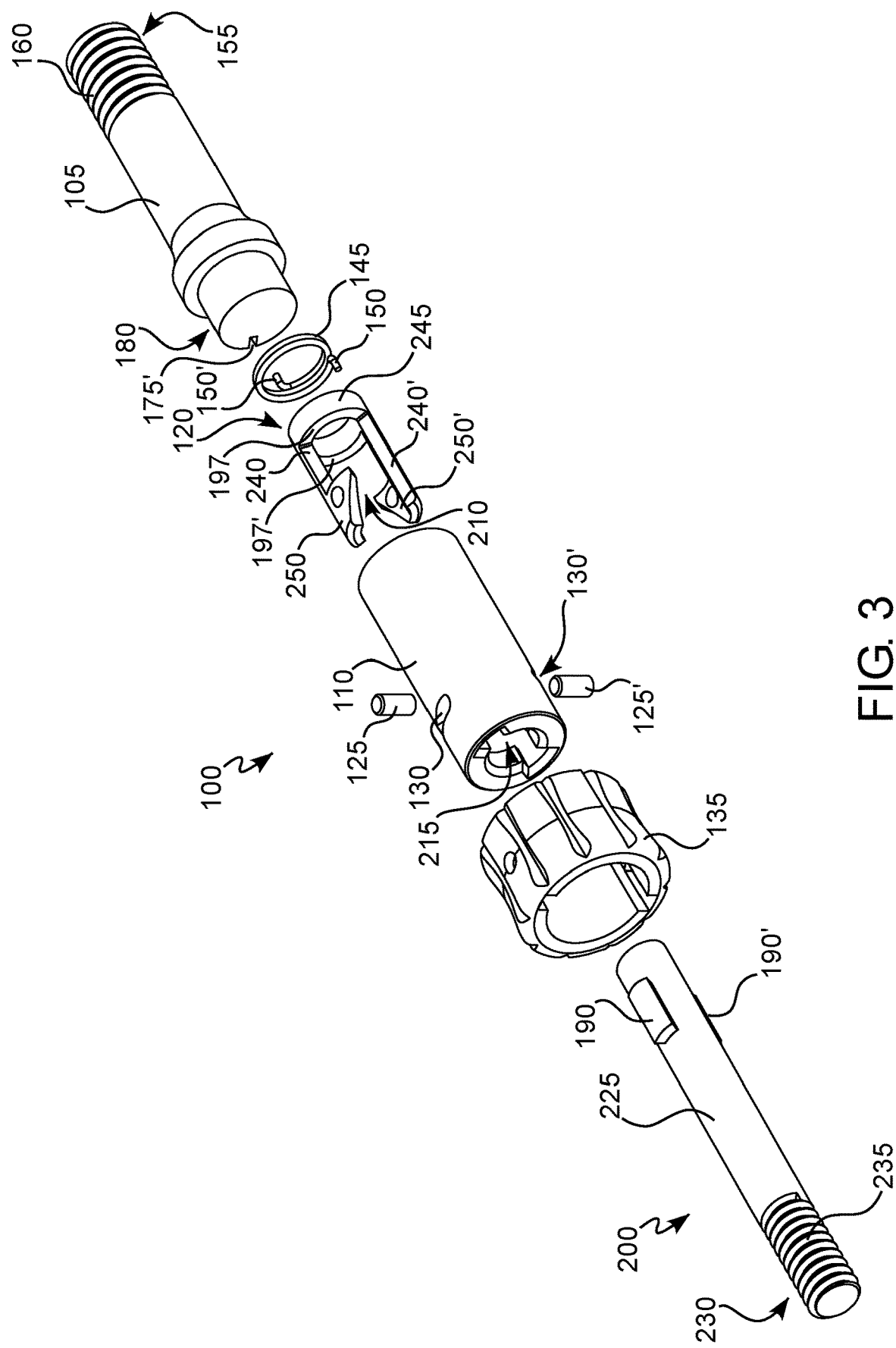
FIG. 3 is an exploded perspective view of the chuck assembly and accessory of FIG. 1.
Figure 4:
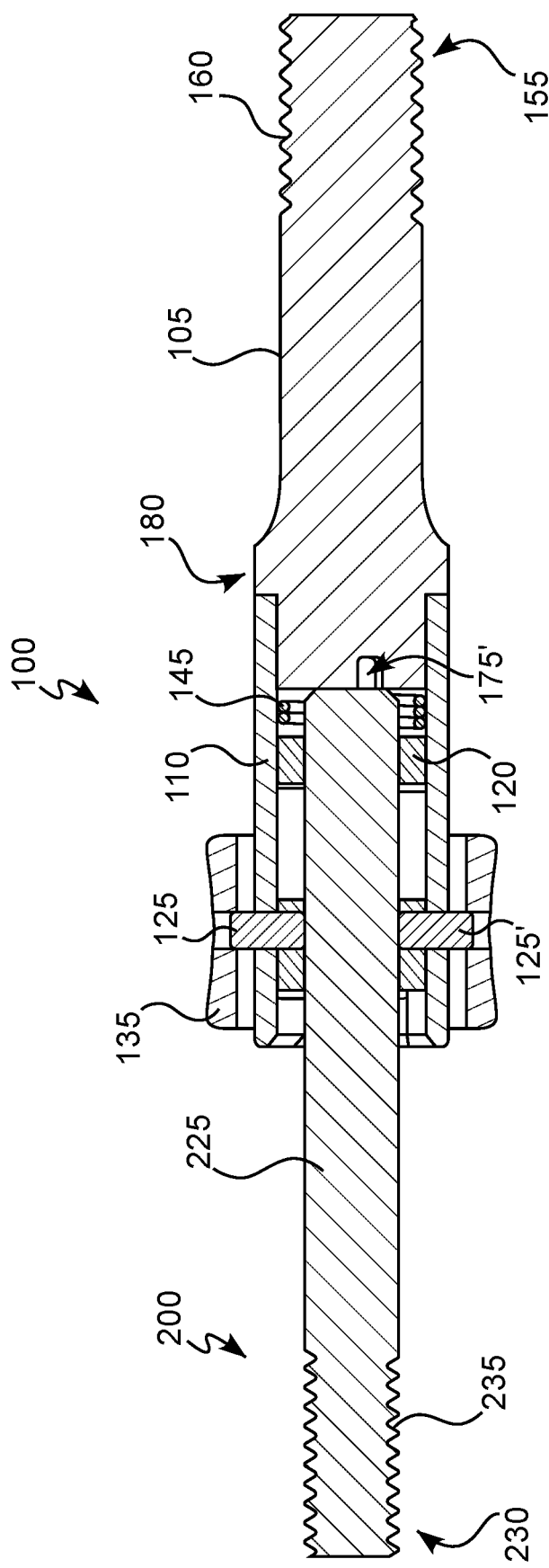
FIG. 4 is a side cross-sectional view of the chuck assembly of FIG. 1 with an inserted accessory.
Figure 5A:
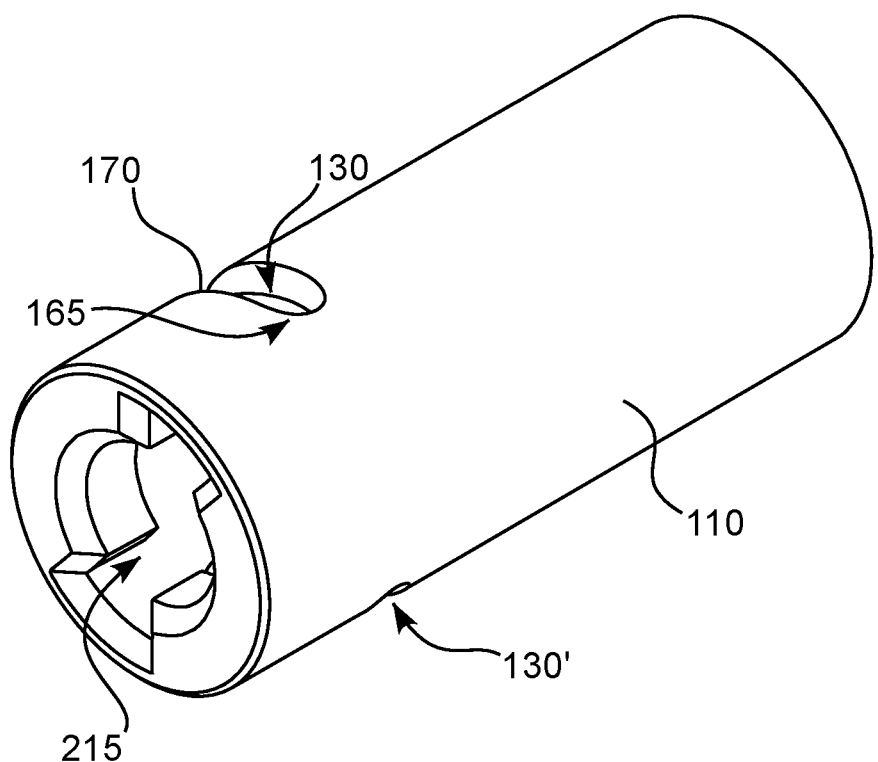
FIG. 5A is a perspective view of a housing of the chuck assembly of FIG. 1.
Figure 5B:
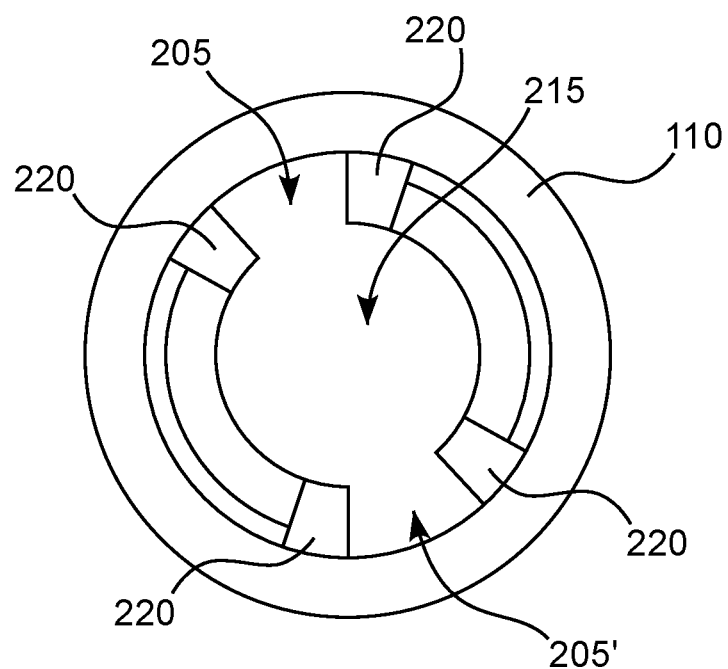
FIG. 5B is a rear view of the housing of FIG. 5A.
Figure 6A:
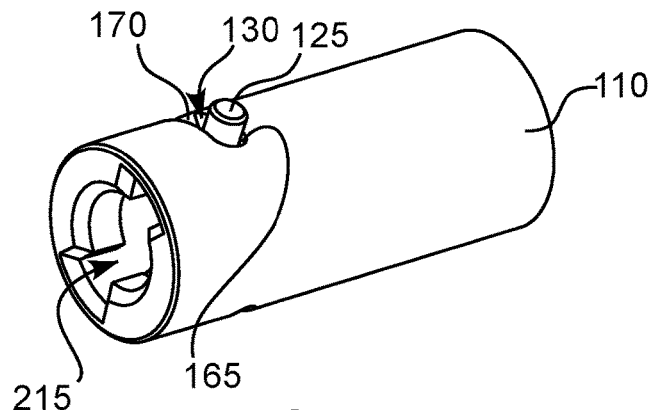
FIG. 6A is a perspective view of the housing of FIG. 5A having an enclosed cam sleeve and stop pins rotated to a locked position.
Figure 6B:
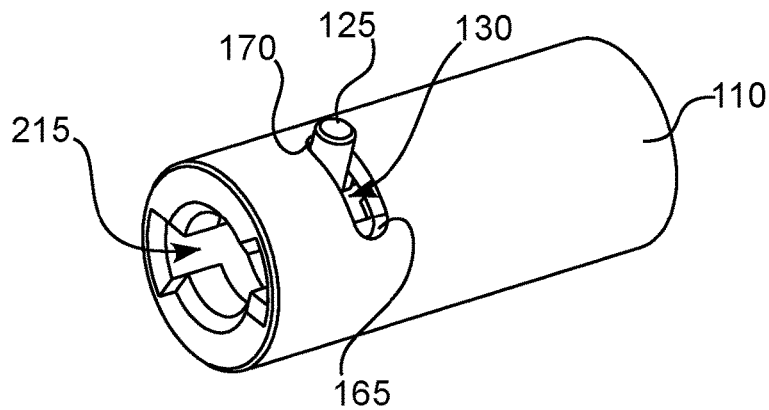
FIG. 6B is a perspective view of the housing of FIG. 5A having an enclosed cam sleeve and stop pins rotated to an unlocked position.
Figure 6C:
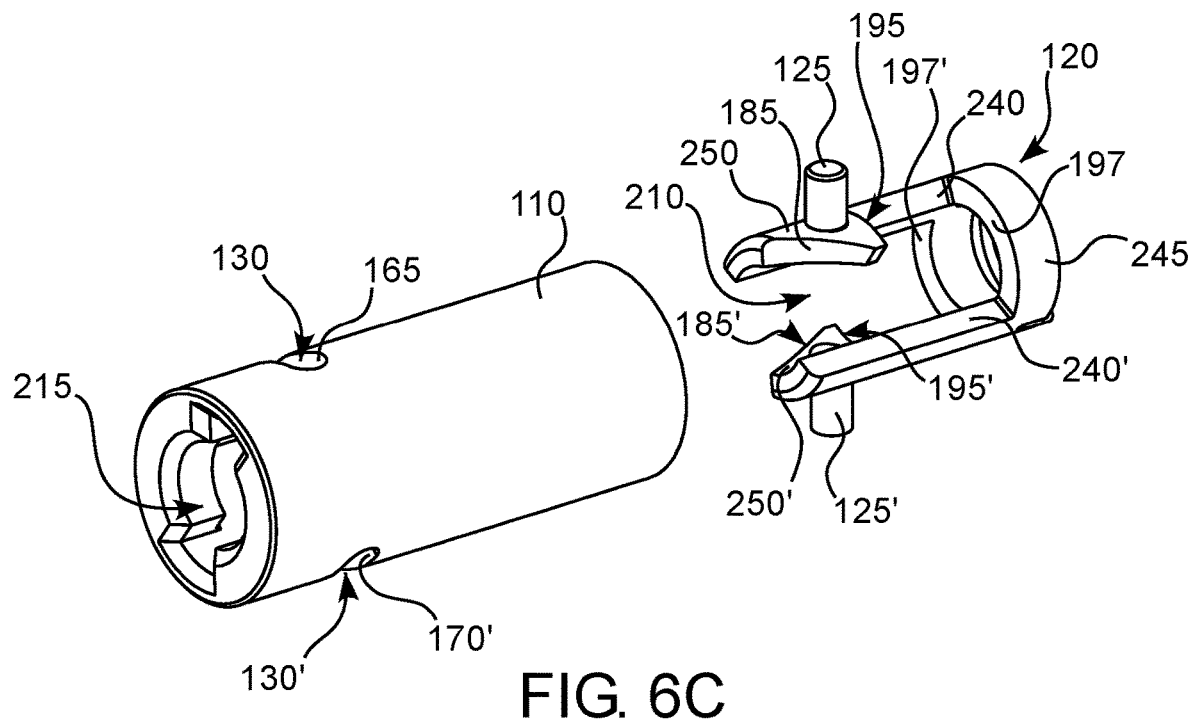
FIG. 6C is a perspective exploded view of the housing, cam sleeve and stop pins of FIGS. 6A and 6B.
Figure 7A:
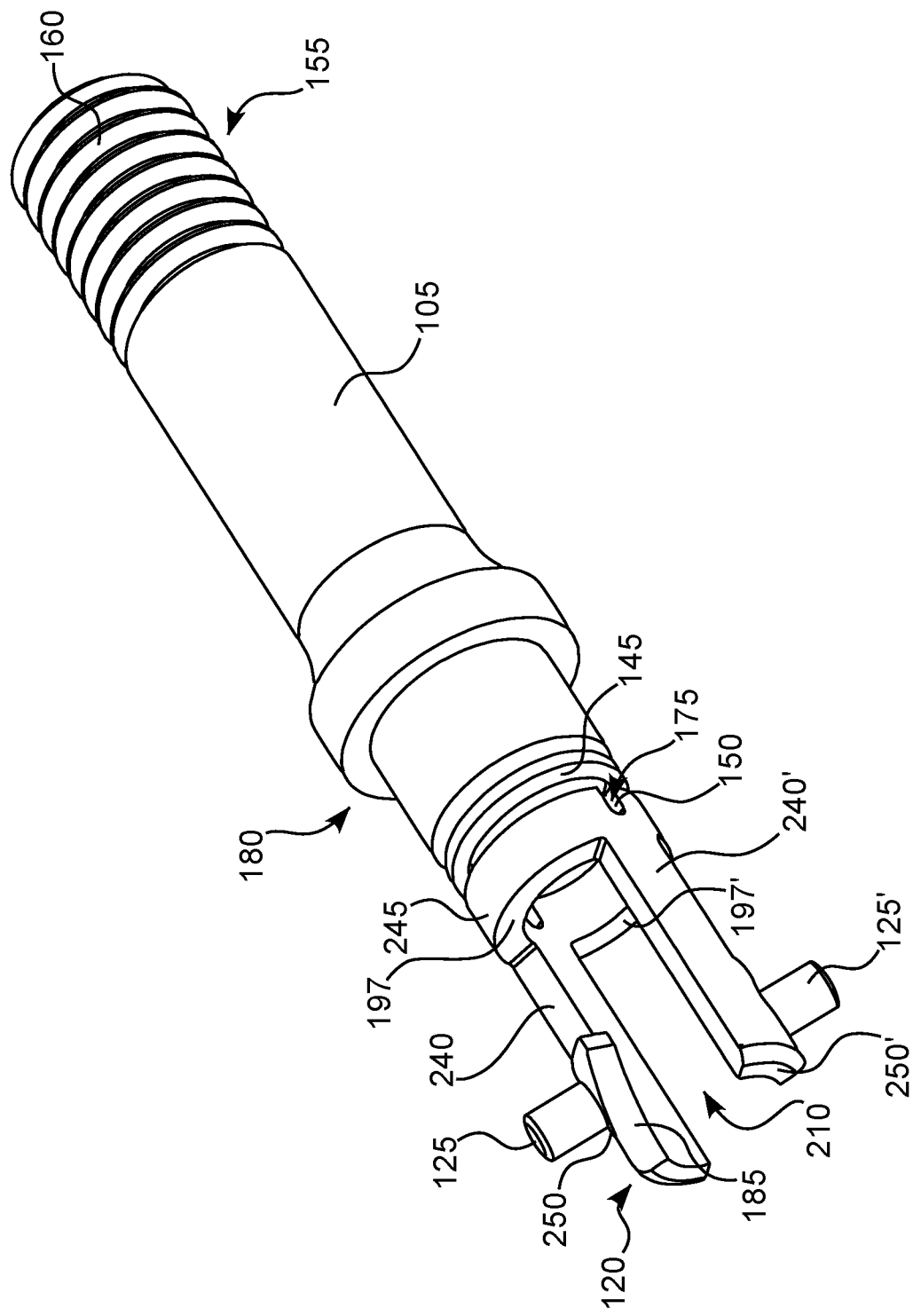
FIG. 7A is a perspective view of a mounting base, a torsion spring, a cam sleeve and stop pins of the chuck assembly of FIG. 1.
Figure 7B:
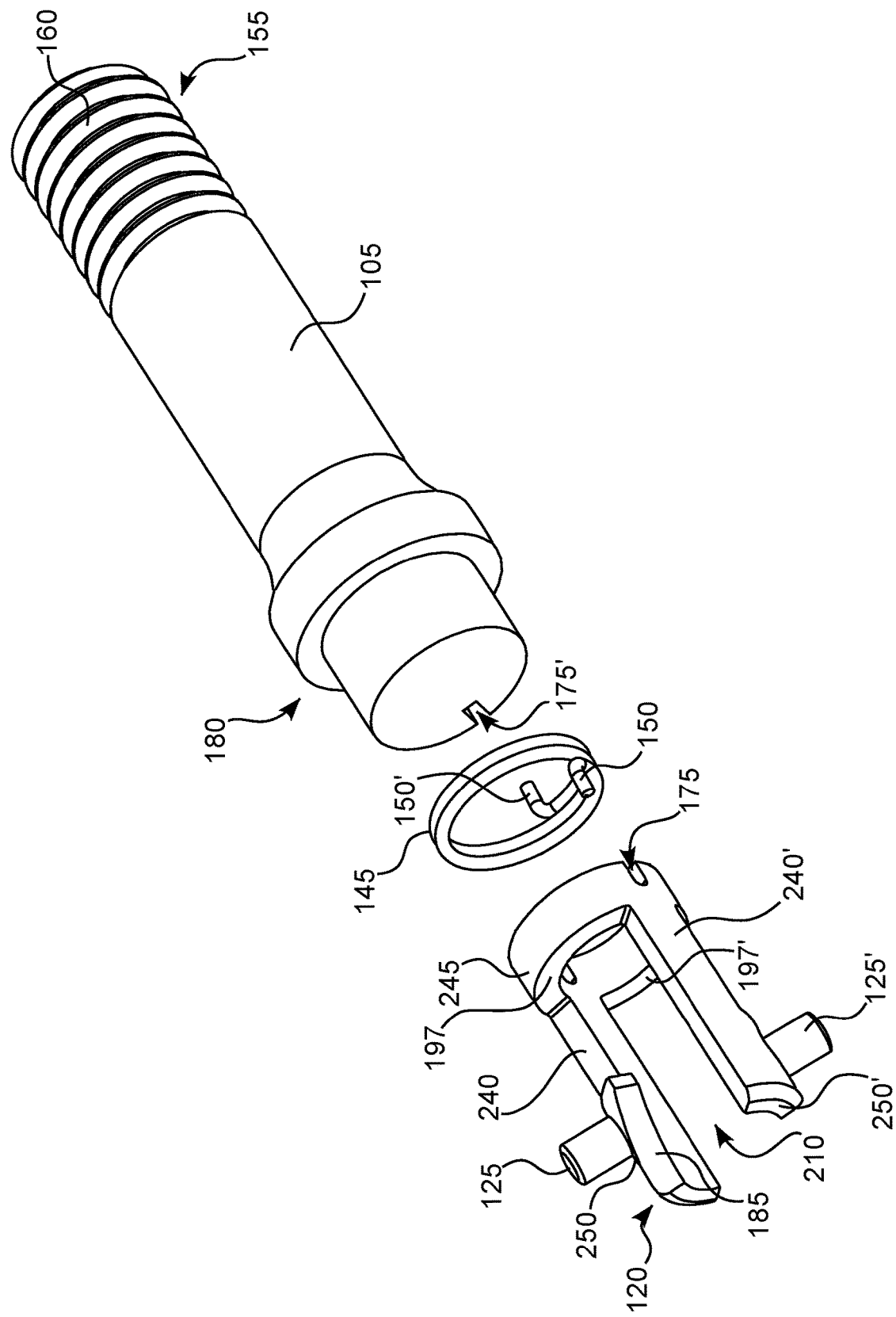
FIG. 7B is a perspective exploded view of the mounting base, torsion spring, cam sleeve and stop pins of FIG. 7A.
Figure 8A:
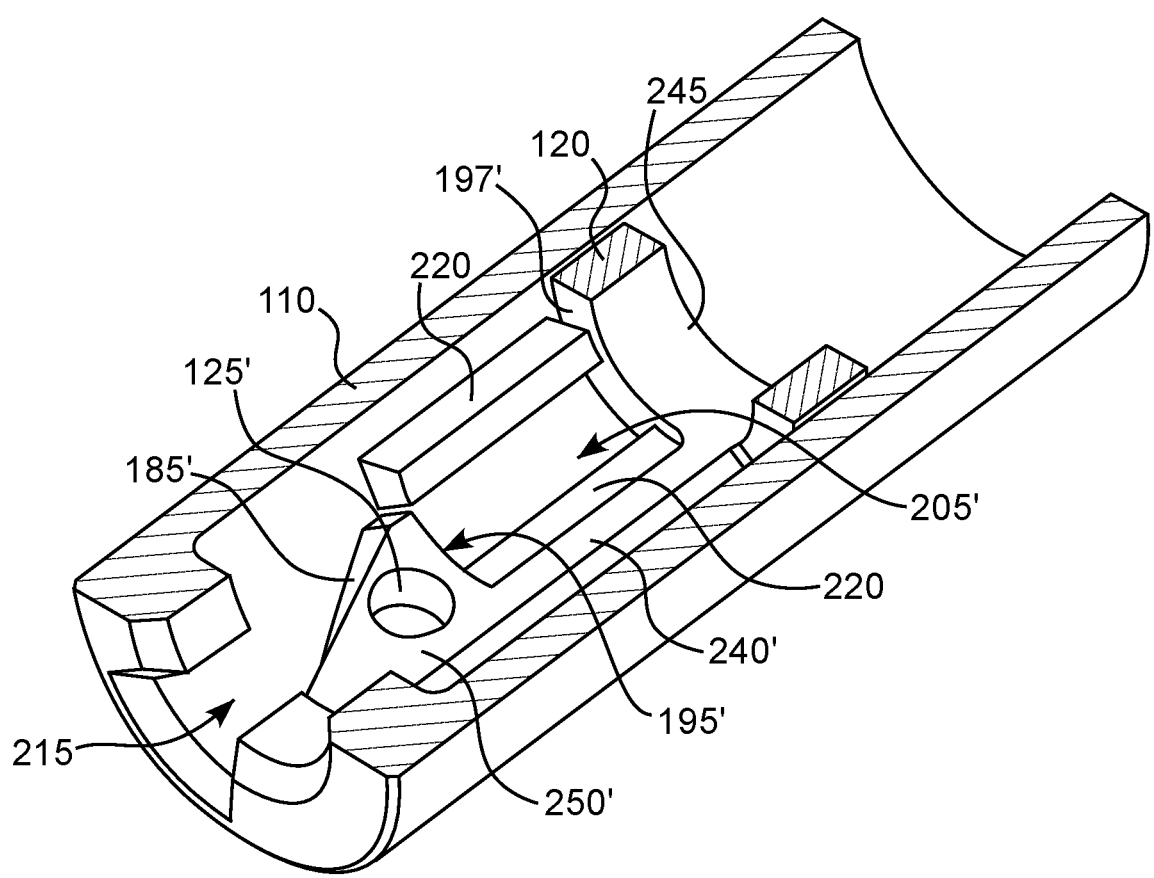
FIG. 8A is a perspective cross-sectional view of a housing and cam sleeve of the chuck assembly of FIG. 1 rotated to a locked position.
Figure 8B:
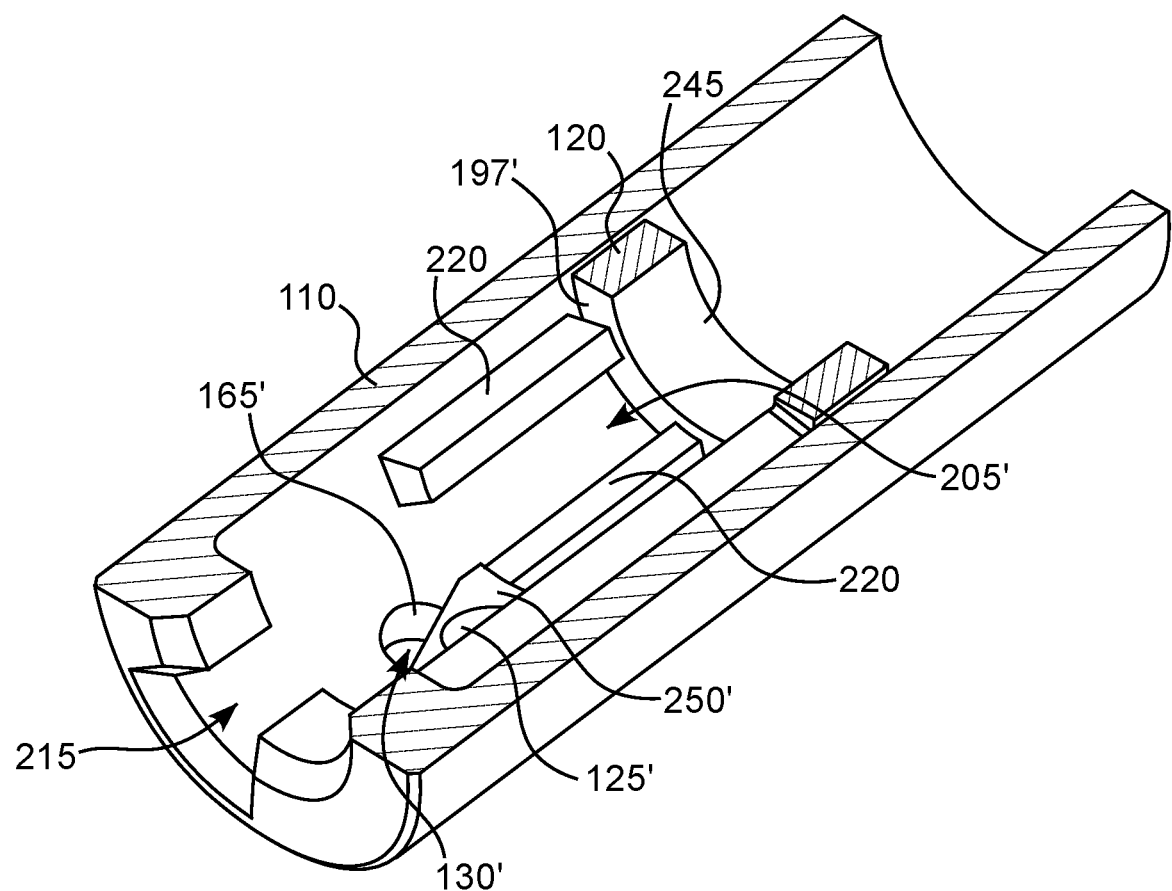
FIG. 8B is a perspective cross-sectional view of the housing and cam sleeve of FIG. 8A rotated to an unlocked position.
Figure 9:
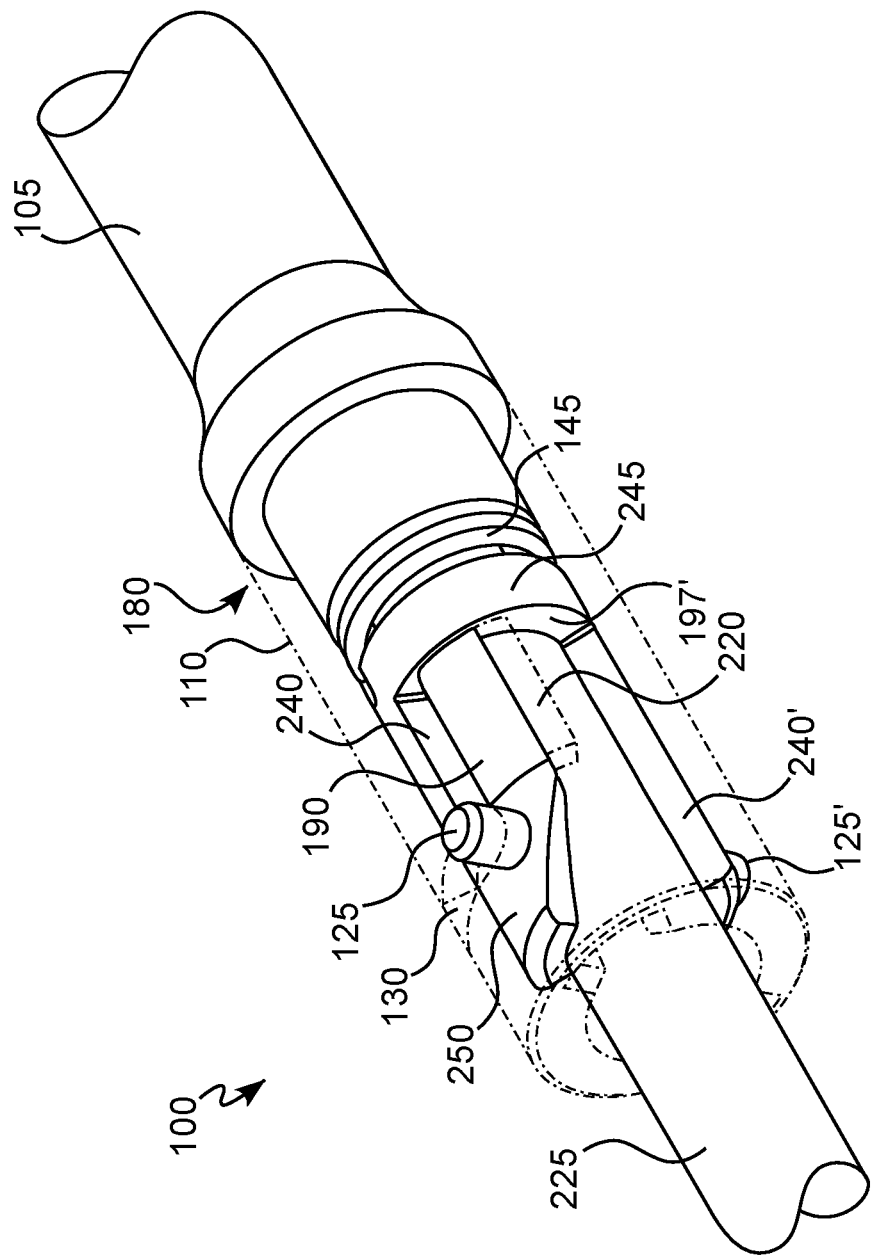
FIG. 9 is a perspective cross-sectional view of the chuck assembly of FIG. 1 with an attached accessory.

As best shown in FIGS. 6A through 6C, the stop pins 125, 125' are coupled to the arms 240, 240' of the cam sleeve 120 and operate to limit the range of rotation of the cam sleeve 120 between a locked position, at which the stop pins 125, 125' respectively engage with the first ends 165, 165' of the stopper slots 130, 130', and an unlocked position, at which the stop pins 125, 125' respectively engage with the second ends 170, 170' of the stopper slots 130, 130'. As shown in FIGS. 3, 7A and 7B, the connecting ends 150, 150' of the biasing member 145 engage respectively with the biasing slots 175, 175' of the cam sleeve 120 and the mounting base 105 to bias the cam sleeve 120 into the locked position. Although the exemplary embodiment depicted in the FIGS. includes the stop pins 125, 125' and the stopper slots 130, 130' for limiting the range of rotation of the cam sleeve 120, it should be appreciated that additional or alternative structures may be provided for limiting the range of rotation, and that various exemplary embodiments of the subject disclosure are not intended to be limited to any particular structure(s). It should also be appreciated that the biasing member 145 (shown as a torsion spring) may be replaced by or supplemented with other biasing structures/members (such as leaf springs or the like) to bias the cam sleeve 120 into the locked position.

To insert and lock the accessory 200 within the chuck assembly 100, the mounting shaft 225 of the accessory 200 is first properly oriented and inserted through the guide slot 215 of the housing 110 and into the central channel 210 of the cam sleeve 120. As the mounting shaft 225 is inserted, the locking tabs 190, 190' respectively engage the camming surfaces 185, 185' of the cams 250, 250', thereby causing the cam sleeve to rotate within housing 110 from the locked position (see FIG. 8A) toward the unlocked position. As insertion of the mounting shaft 225 continues and the cam sleeve 120 reaches the unlocked position (see FIG. 8B), the locking tabs 190, 190' clear the camming surfaces and enter respective locking cavities 205, 205' between the guide rails 220 of the housing. Once the mounting shaft 225 of the accessory 200 is fully inserted to a position at which the locking tabs 190, 190' abut the distally facing locking surfaces 197, 197' of the cam sleeve 120, biasing force produced by the biasing member 145 returns the cam sleeve to the locked position, thereby causing the proximally facing locking surfaces 195, 195' of the cams 250, 250' to close the locking cavities 205, 205' and secure the locking tabs 190, 190' firmly therein. In this manner, the mounting shaft 225 of the accessory is tightly secured within the central channel 210 of the cam sleeve and prevented from rotating or exiting the chuck assembly longitudinally.

To remove the accessory 200 from the chuck assembly 100, the dial 135 is operated manually to rotate the cam sleeve 120 against the biasing force of the biasing member 145 to the unlocked position (see FIG. 8B), thereby retracting the proximally facing locking surfaces 195, 195' from the locking cavities 205, 205' and freeing the locking tabs 190, 190'. The accessory 200 may then be removed longitudinally from the chuck assembly. After the accessory 200 is removed, the dial 135 is released to allow the biasing force of the biasing member 145 to return the cam sleeve 120 to the locked position (see FIG. 8A). The same or other accessory may then be inserted and locked into chuck assembly in a manner similar to that described above.

Due to the construction, size and dimensions of the cams 250, 250' and the guide rails 220, the chuck assembly 100 may withstand high linear loads, such as compression and tension loads, and even higher shock or impact loads (such as, for example, a shock/impact load tension of 2000 lbs), as well as high torsional loads. For example, widening the annular width of the locking tabs 190, 190' and providing the cams 250, 250' with extended proximal locking surfaces 195, 195' allows longitudinal forces exerted on the accessory 200 to spread over a larger surface area at interfaces between the locking tabs 190, 190' and the distally facing locking surfaces 197, 197' (for compression loads) and between the locking tabs 190, 190' and the proximally facing locking surfaces 195, 195' (for tension loads). In similar fashion, the guide rails 220 and the longitudinal length of the locking tabs 190, 190' may be extended to ensure that torsional forces are exerted over a larger surface area at interfaces between the locking tabs 190, 190' and the guide rails 220, thereby increasing the torsional load rating of the chuck assembly 100. This may be desirable, for example, in operations that exert both linear and torsional loads on the chuck assembly 100 in a single operation, such as, for example, when the chuck assembly 100 is used both to twist a threaded extractor into an implant (torsional load) and to thereafter remove the implant via an extraction device coupled to mounting base 105 of the chuck assembly 100 (tensional load).

Various components of the chuck assembly 100 and other chuck assemblies contemplated by the subject disclosure may also be manufactured to provide a low profile. For example, the chuck assembly 100 may include, for example, a mounting base with a cylindrical mounting end having a diameter equal to approximately 0.254, 0.381, 0.508, 0.635, 0.762, 0.889, 1.016, 1.143, or 1.27 cm, a cylindrical housing having a diameter approximately in the range of 0.635, 0.762, 0.889, 1.016, 1.143, 1.27, 1.397, 1.524, 1.651, 1.778, 1.905, or 2.032 cm (with smaller diameters facilitating an impact connection for and allowing compatibility with smaller tools, such as, for example, pins, wires, etc.), and/or a cam sleeve having a central channel sized to receive an accessory mounting shaft having a diameter equal to approximately 0.3175, 0.635, 0.9525, 1.27, or 1.5875 cm. It should be appreciated, however, that various other exemplary embodiments of the subject disclosure are not intended to be limited to any specific component dimensions.

It will be appreciated by those skilled in the art that changes could be made to the exemplary embodiments described above without departing from the broad inventive concept thereof. It is to be understood, therefore, that this disclosure is not limited to the particular exemplary embodiments disclosed, but it is intended to cover modifications within the spirit and scope of the claims defined herein.

I claim:

1. A chuck assembly for a medical device comprising:
a mounting base structured to couple to a tool;
a housing coupled to the mounting base; and
a cam sleeve within the housing and movable with respect to the housing between a locked position and an unlocked position, the cam sleeve having:
an annular base,
an arm extending from the annular base, and
a cam extending laterally from the arm.

2. The chuck assembly of claim 1, wherein the cam includes a distally facing helical camming surface.

3. The chuck assembly of claim 2, wherein the helical camming surface extends annularly about five to twenty degrees.

4. The chuck assembly of claim 1, wherein the cam includes a proximally facing locking surface.

5. The chuck assembly of claim 4, wherein the proximally facing locking surface extends annularly about five to twenty degrees.

6. The chuck assembly of claim 4, wherein the housing includes internal guide rails and the annular base includes a distally facing locking surface, and wherein the proximally facing locking surface, the distally facing locking surface and the guide rails form a cavity for receiving and securing a guide tab of an accessory.

7. The chuck assembly of claim 1, further comprising a biasing member biasing the cam sleeve into the locked position.

8. The chuck assembly of claim 1, wherein the cam sleeve is rotationally movable within the housing.

9. The chuck assembly of claim 1, wherein the cam sleeve includes another arm extending from the annular base.

10. The chuck assembly of claim 1, further comprising a dial engaged with the cam sleeve for moving the cam sleeve between the locked position and unlocked position.

11. The chuck assembly of claim 10, wherein the dial circumscribes the housing.

12. The chuck assembly of claim 1, wherein the housing comprises an overall diameter of about 0.635 to 1.905 cm.

13. The chuck assembly of claim 1, wherein the housing and the cam sleeve are structured to withstand both a torsional load and a linear load.

14. The chuck assembly of claim 13, wherein the linear load includes a tensile load.

15. The chuck assembly of claim 1, wherein the housing is formed integrally with the mounting base.

16. A medical device comprising:
the chuck assembly of claim 1; and
an accessory that includes:
a mounting shaft structured to be received within the housing, and
a mounting tab extending from the shaft and structured to be engaged by and retained within the housing by the cam sleeve.

17. The medical device of claim 16, wherein the mounting tab is a linear tab extending substantially parallel to a longitudinal axis of the mounting shaft.

18. The medical device of claim 16, wherein the mounting shaft includes a working end structured to engage a fixture.

19. The medical device of claim 16, wherein when the accessory is inserted into the housing and the cam sleeve is in the locked position, the mounting tab directly engages the arm.

20. The medical device of claim 16, wherein when the accessory is inserted into the housing and the cam sleeve is in the locked position, the mounting tab is bounded by internal guide rails of the housing, a proximally facing locking surface of the cam and a distally facing locking surface of the annular base.

21. A medical device comprising:
a chuck assembly that includes:
a mounting base structured to couple to a tool,
a housing coupled to the mounting base, and
a cam sleeve within the housing and rotatable with respect to the housing between a locked rotational position and an unlocked rotational position, the cam sleeve having:
an annular base,
a first arm extending from the annular base, the first arm including a first cam extending laterally from the first arm, the first cam having a first distally facing helical camming surface and a first proximally facing locking surface, and
a second arm extending from the annular base and diametrically opposed from the first arm, the second arm including a second cam extending laterally from the second arm, the second cam having a second distally facing helical camming surface and a second proximally facing locking surface; and an accessory releasably engageable with the chuck assembly, the accessory including:
a mounting shaft structured to be received within the housing, and
a mounting tab extending from the mounting shaft and structured to be engaged by and retained within the housing by the cam sleeve.

* * * * *